United States Patent
Matwiejuk et al.

(12) 
(10) Patent No.: US 10,800,802 B2
(45) Date of Patent: Oct. 13, 2020

(54) SEPARATION OF OLIGOSACCHARIDES FROM FERMENTATION BROTH

(71) Applicant: GLYCOM A/S, Hørsholm (DK)

(72) Inventors: Martin Matwiejuk, Hamburg (DE); Markus Jondelius Hederos, Trelleborg (SE)

(73) Assignee: GLYCOM A/S, Hørsholm (DK)

( * ) Notice: Subject to any disclaimer, the term of this patent is extended or adjusted under 35 U.S.C. 154(b) by 241 days.

(21) Appl. No.: 15/703,551

(22) Filed: Sep. 13, 2017

(65) Prior Publication Data

US 2018/0002363 A1 Jan. 4, 2018
US 2019/0345183 A9 Nov. 14, 2019

Related U.S. Application Data

(63) Continuation-in-part of application No. PCT/DK2017/050063, filed on Mar. 7, 2017.

(30) Foreign Application Priority Data

Mar. 7, 2016 (DK) .................................. 2016 70131

(51) Int. Cl.
| | |
|---|---|
| *A23L 33/195* | (2016.01) |
| *B01D 15/36* | (2006.01) |
| *B01D 61/02* | (2006.01) |
| *B01D 61/14* | (2006.01) |
| *B01D 61/16* | (2006.01) |
| *B01D 61/58* | (2006.01) |
| *C07H 1/06* | (2006.01) |
| *C07H 1/08* | (2006.01) |
| *C07H 13/02* | (2006.01) |
| *C07H 13/04* | (2006.01) |
| *C07H 23/00* | (2006.01) |
| *C08B 37/00* | (2006.01) |
| *C12P 19/04* | (2006.01) |
| *C12P 19/18* | (2006.01) |

(52) U.S. Cl.
CPC .............. *C07H 1/08* (2013.01); *A23L 33/195* (2016.08); *B01D 15/362* (2013.01); *B01D 15/363* (2013.01); *B01D 61/027* (2013.01); *B01D 61/142* (2013.01); *B01D 61/145* (2013.01); *B01D 61/16* (2013.01); *B01D 61/58* (2013.01); *C07H 1/06* (2013.01); *C07H 13/02* (2013.01); *C07H 13/04* (2013.01); *C07H 23/00* (2013.01); *C08B 37/0003* (2013.01); *C12P 19/04* (2013.01); *C12P 19/18* (2013.01); *C12Y 204/99* (2013.01); *B01D 2311/06* (2013.01); *B01D 2311/2623* (2013.01); *B01D 2311/2626* (2013.01); *B01D 2311/2688* (2013.01); *B01D 2317/025* (2013.01)

(58) Field of Classification Search
CPC .......... C07H 1/08; C07H 13/02; C07H 23/00; C07H 1/06; C07H 13/04; B01D 15/362; B01D 15/363; B01D 2317/025; B01D 61/027; B01D 61/142; B01D 61/145; B01D 61/16; B01D 61/58; B01D 2311/06; B01D 2311/2623; B01D 2311/2626; B01D 2311/2688; C01D 61/027; C01D 61/145; C01D 61/58; C12P 19/18; C12P 13/02; C12P 19/02; C12P 19/18; C12P 13/02; C12P 19/02; C12P 19/04; C12P 19/26; C12Y 204/99; C12N 9/00; C12N 9/1048; C12N 9/1051; C12N 9/1081; C12N 9/1241; C12N 9/90; C12N 15/62; C07K 2319/00; C07K 2319/02; C07K 2319/20; C07K 2319/21; C07K 2319/41; C07K 2319/92; A23L 33/195
See application file for complete search history.

(56) References Cited

U.S. PATENT DOCUMENTS

| | | | | |
|---|---|---|---|---|
| 5,575,916 | A * | 11/1996 | Brian ................... | A23C 9/1465 210/634 |
| 2002/0034805 | A1* | 3/2002 | Gilbert ..................... | C12N 9/00 435/193 |
| 2002/0148791 | A1* | 10/2002 | DeFrees ............... | B01D 61/022 210/767 |
| 2005/0003499 | A1* | 1/2005 | Keri ........................ | C07C 67/48 435/135 |
| 2007/0020736 | A1 | 1/2007 | Samain | |
| 2008/0145899 | A1* | 6/2008 | Johnson .................. | C12P 13/02 435/97 |
| 2011/0098244 | A1* | 4/2011 | Bonte .................. | A23C 9/1465 514/53 |
| 2012/0208181 | A1* | 8/2012 | Merighi ................... | C12N 9/00 435/6.1 |

FOREIGN PATENT DOCUMENTS

| | | | | |
|---|---|---|---|---|
| CN | 102154163 | | 8/2011 | |
| EP | 1911850 | A1 | 4/2008 | |
| EP | 2408794 | B1 | 5/2013 | |
| EP | 2896628 | A1 * | 7/2015 | ............ A23L 29/30 |
| WO | 9614124 | A1 | 5/1996 | |

(Continued)

OTHER PUBLICATIONS

Machine translation of CN 102154163.*

(Continued)

*Primary Examiner* — Benjamin L Lebron

(74) *Attorney, Agent, or Firm* — Neal, Gerber & Eisenberg LLP

(57) ABSTRACT

The present invention relates to the isolation and purification of sialylated oligosaccharides from an aqueous medium in which they are produced.

25 Claims, No Drawings

(56) References Cited

FOREIGN PATENT DOCUMENTS

| WO | 96/32492 | | 10/1996 |
|---|---|---|---|
| WO | 98/15581 | | 4/1998 |
| WO | 99/31224 | | 6/1999 |
| WO | 01/04341 | A1 | 1/2001 |
| WO | 2006/029538 | A1 | 3/2006 |
| WO | 2006/034225 | A2 | 3/2006 |
| WO | 2007/056191 | A2 | 5/2007 |
| WO | 2007/101862 | A1 | 9/2007 |
| WO | 2009/113861 | A2 | 9/2009 |
| WO | 2010106320 | A2 | 9/2010 |
| WO | 2010/116317 | A1 | 10/2010 |
| WO | 2011/100979 | A1 | 8/2011 |
| WO | 2012/007588 | A9 | 1/2012 |
| WO | 2013/182206 | A1 | 12/2013 |
| WO | 2014/048439 | A1 | 4/2014 |
| WO | 2014/153253 | A1 | 9/2014 |
| WO | 2015106943 | A1 | 7/2015 |
| WO | 2015/188834 | A1 | 12/2015 |
| WO | 2017/101958 | A1 | 6/2017 |
| WO | 2017152918 | A1 | 9/2017 |
| WO | 2019043029 | A1 | 3/2019 |

OTHER PUBLICATIONS

Phillips, T., "Enzymes used in the dairy industry", The Balance. May 14, 2019.*

Dow, "Dowex 22", Feb. (Year: 2009).*

Antoine, T. et al., "Highly Efficient Biosynthesis of the Oligosaccharide Moiety of the GD3 Ganglioside by Using Metabolically Engineered *Escherichia coil*," Angew. Chem. Int. Ed., 2005, vol. 44, pp. 1350-1352.

Chen, X. (2015)."Human Milk Oligosaccharides (HMOS): Structure, Function, and Enzyme-Catalyzed Synthesis," Elsevier Inc. (vol. 72), Advances in Carbohydrate Chemistry and Biochemistry, pp. 113-190. http://dx.doi.org/10.1016/os.accb.2015.08.002.

Drouillard, S. et al., "Efficient synthesis of 6'-sialyllactose, 6'-disialyllactose, and 6'-KDO-lactose by metabolically engineered *E. coli* expressing a multifunctional sialyltransferase from the *Photobacterium* sp. JT-ISH-224," Carbohydrate Research, 2010, vol. 345, pp. 1394-1399.

Fierfort, N. et al., "Genetic engineering of *Escherichia coli* for the economical production of sialylated oligosaccharides," Journal of Biotechnology, 2008, vol. 134, pp. 261-265.

Fort, S. et al., "Biosynthesis of conjugatable saccharidic moieties of GM2 and GM3 gangliosides by engineered *E. coli*," Chem. Commun., 2005, pp. 2558-2560.

Gilbert, M. et al., "The synthesis of sialylated oligosaccharides using a CMP-Neu5Ac synthetase/sialyltransferase fusion," Nature Biotechnology, 1998, vol. 16, pp. 769-772.

International Search Report and Written Opinion dated Mar. 31, 2017 for International Patent Application No. PCT/DK2017/050063 filed on Mar. 7, 2016.

Maru, I. et al., "Synthesis of Sialyllactose from N-Acetylneuraminic Acid and Lactose by a Neuraminidase from Arthrobacter ureafaciens," Biosi. Biotech. Biochem., 1992, vol. 56(10), pp. 1557-1561.

Masuda, M. et al., "Continuous Production of Sialyllactose from Colominic Acid Using a Membrane Reactor," Journal of Bioscience and Bioengineering, 2000, vol. 89(2), pp. 119-125.

Mine, T. et al., "An alpha-2,3-Sialyltransferase from *Photobacterium* sp. JT-ISH-224 Transfers N-Acetylneuraminic Acid to Both the O-2 and O-3' Hydroxyl Groups of Lactose," Journal of Carbohydrate Chemistry, 2010, vol. 29(2), pp. 51-60.

Priem, B. et al., "A new fermentation process allows large-scale production of human milk oligosaccharides by metabolically engineered bacteria," Glycobiology, 2002, vol. 12(4), pp. 235-240.

Ten Bruggencate, S.J. et al., Functional role and mechanisms of sialyllactose and other sialylated milk oligosaccharides, Nutrition Reviews, 2014, vol. 72(6), pp. 377-389.

Urashima, T. et al. (2011) Nutrition and Diet Research Progress: Milk Oligosaccharides. New York: Nova Science Publishers, Inc.

Mitsubishi Chemical Corporation. (2013) Product Line Brochure DIAION [Brochure], 10 pages.

AG® 1-X8 Anion Exchange Resin, analytical grade, 100-200 mesh, chloride form, 500 g #1401441. Retrieved on Jan. 18, 2019, from URL: http://www.bio-rad.com/en-us/sku/1401441-ag-1-x8-anion-exchange-resin-analytical-grade-100-ndash-200-mesh-chloride-form-500-g?ID=1401441 (2 pages).

* cited by examiner

SEPARATION OF OLIGOSACCHARIDES FROM FERMENTATION BROTH

CROSS-REFERENCE TO RELATED APPLICATIONS

This application is a Continuation-in-Part of International Patent Application PCT/DK2017/050063, filed Mar. 7, 2017, which claims the benefit of DK Patent Application PA 2016 70131, filed on Mar. 7, 2016, the contents of both of which are fully incorporated herein by reference.

FIELD OF THE INVENTION

The present invention relates to the isolation and purification of sialylated oligosaccharides from a fermentation broth in which they are produced by a microorganism.

BACKGROUND OF THE INVENTION

During the past decades, the interest in the preparation and commercialisation of human milk oligosaccharides (HMOs) has been increasing steadily. The importance of human milk oligosaccharides is directly linked to their unique biological activities. Sialylated human milk oligosaccharides such as disialyllacto-N-tetraose, 3'-O-sialyl-3-O-fucosyllactose, sialyllactose, 3'-O-sialyllactose, 6'-O-sialylated-lacto-N-neotetraose and 3'-O-sialylated-lacto-N-tetraose, are among the major components of human milk. In these sialylated human milk oligosaccharides the sialic acid residue is always linked to the 3-O- and/or 6-O-position of a terminal D-galactose or to the 6-O-position of a non-terminal GlcNAc residue via α-glycosidic linkages. Sialylated HMOs are thought to have significant health benefits for the neonate, because of their roles in supporting resistance to pathogens, gut maturation, immune function and cognitive development (ten Bruggencate et al. *Nutr. Rev.* 72, 377 (2014)).

Efforts to develop processes for synthesizing HMOs, including sialylated HMOs, have increased significantly in the last ten years due to their roles in numerous human biological processes. In this regard, processes have been developed for producing them by microbial fermentations, enzymatic processes, chemical syntheses, or combinations of these technologies. With regard to productivity fermentation processes, on a lab scale, to produce 3'-SL and 6'-SL have proved to be promising.

However, to isolate sialylated lactoses or sialylated oligosaccharides from a complex matrix such as a fermentation broth is a challenging task. Antoine et al. *Angew. Chem. Int. Ed.* 44, 1350 (2005) and US 2007/0020736 disclosed the production of 3'-SL, and accompanying di- and trisialylated lactoses by a genetically modified *E. coli*; the broth containing approx. 0.8 mM 3'-SL was treated as follows: adsorption of the products from the centrifuged supernatant on charcoal/celite, washing away the water soluble salts with distilled water, eluting the compounds by gradient aqueous ethanol, separation of the sialylated products on a Biogel column and desalting, leading to 49 mg of 3'-SL from 1 litre of broth. WO 01/04341 and Priem et al. *Glycobiology* 12, 235 (2002) disclosed the production of 3'-SL by a genetically modified *E. coli*; 3'-SL was isolated by the following sequence of operations: heat permeabilization of the producing cells followed by centrifugation, adsorption of the product from the supernatant on charcoal/celite, washing away the water soluble salts with distilled water, eluting the compound by gradient aqueous ethanol, binding the compound to a strong anion exchanger in $HCO_3^-$-form, elution of the compound with a linear gradient $NaHCO_3$-solution, then eliminating the sodium bicarbonate with a cation exchanger (in $H^+$-form), resulting in isolated 3'-SL with 49% purification yield. WO 2007/101862 and Fierfort et al. *J. Biotechnol.* 134, 261 (2008) disclosed an alternative work-up procedure of a 3'-SL fermentation broth, the procedure comprising the steps of heat permeabilization of the producing cell, centrifugation, adjusting the pH of the extracellular to 3.0 by the addition of a strong cation exchanger resin in acid form, removal of the precipitated proteins by centrifugation, adjusting the pH of the supernatant to 6.0 by the addition of a weak anion exchanger in base form, binding the sialyllactose to an anion exchanger in $HCO_3^-$-form, after washing with distilled water, elution of the compound with a continuous gradient $NaHCO_3$-solution, eliminating the sodium bicarbonate with a cation exchanger (in $H^+$-form) until pH 3.0 was reached, then adjustment of the pH to 6.0 with NaOH. The above purification allowed to isolate 15 g of 3'-SL from 1 litre of broth containing 25.5 g of 3'-SL. Drouillard et al. *Carbohydr. Res*, 345, 1394 (2010)) applied Fierfort's procedure above to a fermentation broth containing 6'-SL (11 g/l) and some 6,6'-disialyllactose (DSL), and thus isolated 3.34 g 6'-SL+DSL in a ratio of 155/86.

WO 2006/034225 describes two alternative purifications of 3'-SL from a producing fermentation broth. According to the first procedure, the lysate from the culture was diluted with distilled water and stirred with activated charcoal/celite. The slurry was washed with water, then the product was eluted from the charcoal/celite with aq. ethanol. According to the second method, the culture cells were heat treated and the precipitated solids were separated from the supernatant by centrifugation. The resulting supernatant was processed through a microfilter, the permeate was passed through a 10 kDa membrane, then nanofiltered. The resulting retentate was then diafiltered to collect the final sample. Both purification methods provided 90-100 mg 3'-SL from 1 litre of fermentation broth.

Both Gilbert et al. *Nature Biotechnol.* 16, 769 (1998) and WO 99/31224 disclose the enzymatic production of 3'-SL starting from lactose, sialic acid, phosphoenolpyruvate, ATP and CMP using a CMP-Neu5Ac synthetase/α-2,3-sialyl transferase fusion protein extract. The product was purified by a sequence of ultrafiltration (3000 MWCO), C18 reverse phase chromatography, nanofiltration/diafiltration at pH-3 and pH=7, acidification with a strong cation exchange ($H^+$) resin, neutralization with NaOH solution and active charcoal decolourization.

WO 2009/113861 discloses a process for isolating sialyllactose from defatted and protein-free milk stream, comprising contacting said milk stream with a first anion exchange resin in the free base form and having a moisture content of 30-48% so that the negatively charged minerals are bound to the resin and the sialyllactose is not, followed by a treatment with a second anion exchange resin in the free base form which is a macroporous or gel type resin and has a moisture content between 50 and 70% so that the sialyllactose is bound to the resin. In this process, the sialyllactose containing stream is rather diluted (a couple of hundreds ppm of concentration) and the sialyllactose recovery from the first resin is moderate.

The drawback of the above sialyllactose purification processes is the poor to moderate purification yield and/or the non-satisfactory product purity. Thus, simpler and/or more effective ways for isolating and purifying these products from aqueous media such as a fermentation broth on an industrial scale have been sought.

SUMMARY OF THE INVENTION

The invention relates to a method for separating and purifying a sialylated oligosaccharide from an aqueous medium, the aqueous medium being a fermentation broth or an enzymatic reaction mixture containing said sialylated oligosaccharide which aqueous medium can optionally be pre-treated, comprising a treatment of said aqueous medium or said pre-treated aqueous medium with a strong anion exchange resin and a strong cation exchange resin.

Preferably, the strong anion exchange resin is in chloride ($Cl^-$) from and the strong cation exchange resin is in protonated ($H^+$) or alkali metal ion ($M^+$) form. When the strong cation exchange resin is in protonated form, the eluate after the strong cation exchange treatment is neutralized with an alkali metal ion containing base or its solution, preferably with alkali metal hydroxide. The preferred alkali metal ion is sodium ion.

Accordingly, the invention relates to a method or process for separating a sialylated oligosaccharide/sialylated lactose from an aqueous medium, the method comprising treating said aqueous medium containing said sialylated oligosaccharide/sialylated lactose with a strong anion exchange resin in CF-form and a strong cation exchange resin. Moreover, the invention relates to a method or process for separating a sialylated oligosaccharide/sialylated lactose from an aqueous medium, the method comprising pre-treating the aqueous medium, e.g. via ultrafiltration, nanofiltration, active charcoal treatment, or a combination thereof, to result in an aqueous solution containing said sialylated oligosaccharide, and treating the aqueous solution with a strong anion exchange resin in $Cl^-$-form and a strong cation exchange resin.

In one embodiment, the separation/purification method further comprises a step of
  ultrafiltration (UF), preferably to separate biomass and or enzymes from the aqueous medium,
  nanofiltration (NF), preferably to concentrate the sialylated oligosaccharide in the aqueous medium and/or reduce an inorganic salt content of the aqueous medium, and/or
  activated. charcoal (AC) treatment, preferably to decolorize the aqueous medium.

Preferably, the UF step is performed before any of the NF and AC steps and the ion exchange resin treatment. The NF and AC steps and the ion exchange resin treatment can be conducted in any order. The sialylated oligosaccharide can be collected after any of the NF and AC steps and the ion exchange resin treatment.

Also preferably, the aqueous medium is a fermentation broth of culturing a genetically modified microorganism capable of producing said sialylated oligosaccharide from an internalized carbohydrate precursor.

Also preferably, the method is carried out, applied on an aqueous medium containing a sialylated oligosaccharide, in the following sequence: UF step, NF step, optional AC treatment and treatment with a strong anion exchange resin and a strong cation exchange resin.

One embodiment the invention relates to a method for separating and purifying a sialylated oligosaccharide from a fermentation broth, wherein said sialylated oligosaccharide is produced by culturing a genetically modified microorganism capable of producing said sialylated oligosaccharide from an internalized carbohydrate precursor, comprising the steps of:
  a) ultrafiltration (UF) of the fermentation broth and collecting the UF permeate (HP),
  b) nanofiltration (NF) of the UFP and collecting the NF retentate (NFR),
  c) optionally, treating the UFP and/or NFR with activated charcoal, and collecting the charcoal eluate (CE), and
  d) treating the UFP, NFR and/or CE with a strong anion exchange resin and a strong cation exchange resin as disclosed above.

The steps c) and d) can be conducted in any order. Preferably all of the steps a) to d) are conducted, more preferably in the following order: step a), step b), step c), step d).

DETAILED DESCRIPTION OF THE INVENTION

1. Terms and Definitions

In accordance with this invention, the term "sialylated oligosaccharide" preferably means a sugar polymer containing at least two monosaccharide units, at least one of which is a sialyl (N-acetylneuraminyl) moiety. The sialylated oligosaccharide can have a linear or branched structure containing monosaccharide units that are linked to each other by interglycosidic linkage. Advantageously, the sialylated oligosaccharide is an acidic human milk oligosaccharide.

The term "acidic human milk oligosaccharide" or "acidic HMO" preferably means a complex carbohydrate found in human breast milk (Urashima et al.: *Milk Oligosaccharides*. Nova Science Publishers, 2011; Chen *Adv. Carbohydr. Chem. Biochem.* 72, 113 (2015)) comprising a core structure being a lactose unit at the reducing end that can be elongated by one or more β-N-acetyl-lactosaminyl and/or one or more β-lacto-N-biosyl units, and which core structure is substituted by an α-N-acetyl-neuraminyl (sialyl) moiety and optionally can be substituted by an α L-fucopyranosyl moiety. In this regard, the acidic HMOs have at least one sialyl residue in their structure. Examples of acidic HMOs include 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), LST c, fucosyl-LST c (FLST c), sialyl-LNH (SLNH), sialyl-lacto-N-hexaose (SLNH), sialyl-facto-N-neohexaose I (SLNH-I), sialyl-lacto-N-neohexaose II (SLNH-II) and disialyl-lacto-N-tetraose (DS-LNT).

The term "genetically modified cell" or "genetically modified microorganism" preferably means a cell or a microorganism, such as a bacterial cell, e.g. an *E. coli* cell, in which there is at least one alteration in its DNA sequence. The alteration can result in a change in the original characteristics of the wild type cell, e.g. the modified cell is able to perform additional chemical transformation due to the introduced new genetic material that encodes the expression of an enzymes not being in the wild type cell, or is not able to carry out transformation like degradation due to removal of gene/genes (knockout). A genetically modified cell can be produced in a conventional manner by genetic engineering techniques that are well-known to those skilled in the art.

The term "genetically modified cell or microorganism capable of producing a sialylated oligosaccharide from an internalized carbohydrate precursor" preferably means a cell or a microorganism which is genetically manipulated (vide supra) to comprise a recombinant gene encoding a sialyl transferase necessary for the synthesis of said sialylated oligosaccharide, a biosynthetic pathway to produce a sialic acid nucleotide donor suitable to be transferred by said glycosyl transferase to a carbohydrate precursor (acceptor) and/or a mechanism of internalization of a carbohydrate precursor (acceptor) from the culture medium into the cell where it is sialylated to produce the sialylated oligosaccharide of interest.

The term "aqueous medium containing a sialylated oligosaccharide" preferably means an aqueous reaction or production mixture in which said sialylated oligosaccharide is produced or synthesized, and said aqueous reaction or production mixture is obtained at the end of the reaction or production. Accordingly, the aqueous medium typically contains besides the sialylated oligosaccharide as primary product-by-products of different kinds, unreacted reactants or reagents, intermediates, catalysts, additives, solvents (other than water), etc., depending on the nature of the synthesis reaction or production method.

The term "aqueous solution containing a sialylated oligosaccharide" preferably means and optionally pre-treated aqueous medium containing said sialylated oligosaccharide (vide supra) that is subjected to ion exchange resin treatment according to this invention. In this regard, the aqueous medium containing a sialylated oligosaccharide can either be directly subjected to ion exchange resin treatment according to the present invention, or that aqueous medium is pre-treated by one or more steps different than ion exchange treatment according to the present invention before applying the ion exchange resin treatment according to the present invention. In the sense of the above definition, the term "aqueous solution containing a sialylated oligosaccharide" embraces aqueous medium containing said sialylated oligosaccharide and the pre-treated aqueous medium containing said sialylated oligosaccharide. By way of pre-treatment, the aqueous medium is partially purified so that the amounts of some contaminants are reduced.

The term "around" means, in one embodiment, ±10% deviation from the value indicated, or in another embodiment, ±5% deviation.

2. Method for Separating Sialylated Oligosaccharides

The invention relates to a method for separating a sialylated oligosaccharide/sialylated lactose from other compounds present in an aqueous medium, e.g. in a fermentation broth obtained by culturing a genetically modified cell or microorganism capable of producing said sialylated oligosaccharide/sialylated lactose from an internalized carbohydrate precursor or in an enzymatic reaction mixture.

The method of the invention provides a solution that is highly enriched with the sialylated oligosaccharide/sialylated lactose from which solution the sialylated oligosaccharide/sialylated lactose can be obtained in high yield, in uniform salt form, preferably in the form of a sodium salt, and with good purity, especially with very low inorganic anion, preferably multivalent anion, content and low amino acid and organic amine content.

2.1 Application of Ion Exchange Resins in improving the Purification/Separation of Sialylated Oligosaccharides It has been discovered that an efficient and high yielding purification/separation of a sialylated oligosaccharide/sialylated lactose is achievable without binding the sialylated oligosaccharide/sialylated lactose to an anion exchange resin, contrary to the prior art hints.

Accordingly, an aqueous medium containing sialylated oligosaccharide/sialylated lactose, obtained preferably after fermentation or ex vivo enzymatic reaction, and optionally pre-treated by membrane filtration and/or clarified by active charcoal treatment, is subjected a strong cation exchange resin treatment, wherein the strong cation exchange resin is either a) in salt form, more preferably the salt form is of a monovalent alkaline cation such as $Na^+$ or $K^+$, or b) in $H^+$-form.

In embodiment a), cations of the load solution containing the sialylated oligosaccharide/sialylated lactose are exchanged by the alkaline cation (e.g. $Na^+$ or $K^+$) of the resin to provide directly the corresponding alkaline salt of the sialylated oligosaccharide/sialylated lactose in the eluate without the need of pH-adjustment suggested by the prior art.

In embodiment b), the eluate of the resin treatment contains the sialylated oligosaccharide/sialylated lactose in protonated form, which is immediately neutralized by addition of an alkaline solution to the eluate to obtain an alkaline salt of the sialylated oligosaccharide.

In both cases, the recovery yield of this step is more than 95%, even near to quantitative. Excess of the monovalent alkaline cations can be removed in a diafiltration step, for example using a nanofiltration membrane, to further improve the purity of the isolated sialylated oligosaccharide/sialylated lactose salt. The application of anion exchange resin in $HCO_3^-$-form suggested by the prior art is avoidable, which is beneficial in industrial scale operation with regard to feasibility, because the bicarbonate removal by acidification would liberate a significant amount of carbon dioxide gas which would require extra security and technical measures.

The above ion exchange resin treatment step contributes so to the purity of the isolated sialylated oligosaccharide/sialylated lactose salt that its assay (assessed by NMR) can be as high as 90%, even as high as 91%.

Moreover, the present inventors discovered that this high assay can be further improved by an efficient removal of multivalent anions such as sulphate, phosphate or orthophosphate and/or organic amines and/or amino acids and/or short water soluble peptides, meanwhile the purification/isolation yield remains at least as high as before.

Accordingly, the present invention relates to a method for separating and/or purifying a sialylated oligosaccharide/sialylated lactose from an aqueous medium, comprising a treatment of said aqueous medium or a pre-treated aqueous medium with a strong anion exchange resin in chloride ($Cl^-$) form and a strong cation exchange resin. The aqueous medium containing a sialylated oligosaccharide/sialylated lactose is a medium in which said sialylated oligosaccharide/sialylated lactose has previously formed or produced by chemical, enzymatic or any other way. Typically, the aqueous medium containing a sialylated oligosaccharide/sialylated lactose is typically a fermentation broth or an enzymatic reaction milieu/mixture, preferably a fermentation broth. The strong cation exchange resin is in protonated ($H^+$) or alkali metal ion ($M^+$) form. When the strong cation exchange resin is in protonated form, the eluate after the strong cation exchange treatment is neutralized with an alkali metal ion containing base, preferably with an alkali metal hydroxide. The preferred alkali metal ion is sodium ion.

The aqueous medium containing the sialylated oligosaccharide/sialylated lactose and preferably obtained after fermentation or ex vivo enzymatic reaction can be directly subjected to the above disclosed ion exchange resin treatment, but preferably pre-treated before the ion exchange resin treatment as disclosed later. The aqueous medium and the pre-treated aqueous medium together are referred to as an aqueous solution containing the sialylated oligosaccharide/sialylated lactose.

The application of a strong anion exchange resin in chloride (Cl⁻) form ensures that the mono- and multivalent inorganic anions present in the aqueous medium are efficiently exchanged to chloride ions by binding the inorganic anions different than chloride to the resin. The sialylated oligosaccharide/sialylated lactose anion does not, or at least practically not, bind to the ion exchange resin in chloride form. Therefore the resin eluate contains the sialylated oligosaccharide/sialylated lactose and exclusively chloride ions as anions, the latter can be removed from the obtained eluate in a subsequent step e.g. by diafiltration during nanofiltration giving a solution that contains substantially no or at least a very low level of inorganic anions. Furthermore, a strong anion exchange resin in chloride (Cl⁻) form has a decolourization effect, thus lower amount of active charcoal may be necessary for an optional precedent or subsequent clarification step. In addition, a strong anion exchange resin in chloride (Cl⁻) form very efficiently removes amino acids, short peptides and organic amines from the feed solution.

In one embodiment, the strong cation exchange resin is in alkali metal ion (M⁺) form. Its application ensures that the inorganic cations present in the aqueous medium are efficiently exchanged to the alkali metal ion, therefore the alkali metal ion salt of the sialylated oligosaccharide/sialylated lactose is obtained. The alkali metal ion is preferably sodium ion.

In other embodiment, the strong cation exchange resin is in protonated (H⁺) form. In addition to binding the inorganic cation present in the feed solution, organic amines optionally made metabolically during the fermentation by the utilized production strain, amino acids and short peptides are efficiently bound and removed. The obtained resin eluate, containing the sialylated oligosaccharide/sialylated lactose in acidic form, is then immediately neutralized by addition of an alkali metal ion containing base, preferably an alkali metal hydroxide, thus forming the alkali metal salt of the sialylated oligosaccharide/sialylated lactose.

The strong cation and anion resins disclosed above can be applied in any order. However, it is more preferred when the strong cation resin treatment follows the strong anion resin treatment. This resin setup is technically advantageous, because the eluate from the strong anion exchange resin in chloride (Cl⁻) can be directly a feed for the strong cation exchange (H⁺) treatment. In reverse order, the two resin treatments are separated by a neutralization step.

The recovery yield of the sialylated oligosaccharide/sialylated lactose in the treatment with strong anion and cation exchange resins as disclosed above is at least 90% (90% and above), preferably at least 92% (92% and above).

In this dual ion exchange resin treatment step, the degree of crosslinking in the applied ion exchange resins can be chosen depending on the operating conditions of the ion exchange column. A highly crosslinked resin offers the advantage of durability and a high degree of mechanical integrity, however suffers from a decreased porosity and a drop off in mass-transfer. A low-crosslinked resin is more fragile and tends to swell by absorption of mobile phase. The particle size of the ion exchange resin is selected to allow an efficient flow of the eluent, while the charged materials are still effectively removed. A suitable flow rate may also be obtained by applying a negative pressure to the eluting end of the column or a positive pressure to the loading end of the column, and collecting the eluent. A combination of both positive and negative pressure may also be used.

Non-limiting examples of a suitable acidic cation exchange resin can be e.g. Amberlite IR100, Amberlite IR120, Amberlite FPC22, Dowex 50WX, Finex CS16GC, Finex CS13GC, Finex CS12GC, Finex CS11GC, Lewatit S, Diaion SK, Diaion UBK, Amberjet 1000, Amberjet 1200.

Non-limiting examples of a suitable basic anion exchange resin can be e.g. Amberjet 4200, Amberjet 4600, Amberlite IR400, Amberlite IR410, Amberlite IR458, Diaion SA, Diaion UBA120, Lewatit MonoPlus M, Lewatit S7468.

2.2 Pre-Treatment of an Aqueous Medium Containing a Sialylated Oligosaccharide/Sialylated Lactose Before Ion Exchange Resin Treatment: Ultrafiltration Once the sialylated oligosaccharide/sialylated lactose is produced either by fermentation or an ex vivo enzymatic process, the aqueous medium containing the sialylated oligosaccharide/sialylated lactose is pre-treated before ion exchange treatment, e.g. subjected to ultrafiltration, preferably as a first step. A fermentation broth typically contains, besides the sialylated oligosaccharide/sialylated lactose produced, the biomass of the cells of the used microorganism together with proteins, protein fragments, DNA, endotoxins, biogenic amines, inorganic salts, unreacted carbohydrate acceptor such as lactose, sugar-like by-products, sialic acid, colorizing bodies, etc. An ex vivo enzymatic reaction mixture typically contains, besides the sialylated oligosaccharide/sialylated lactose produced, proteins, protein fragments, inorganic salts, unreacted carbohydrate acceptor such as lactose, sugar-like by-products, sialic acid and its precursors, etc. The ultrafiltration step is to separate the biomass and high molecular weight suspended solids from the soluble components of the aqueous medium which pass through the ultrafiltration membrane in the permeate. This UF permeate (UFP) is an aqueous solution containing the produced sialylated oligosaccharide/sialylated lactose.

Any conventional ultrafiltration membrane can be used having a molecular weight cut-off (MWCO) range between about 1 and about 500 kDa, such as 10-250, 50-100, 200-500, 100-250, 1-100, 1-50, 10-25, 1-5 kDa, any other suitable sub-ranges. The membrane material can be a ceramic or made of a synthetic or natural polymer, e.g. polysulfone, polypropylene, cellulose acetate or polylactic acid. The ultrafiltration step can be applied in dead-end or cross-flow mode. This UF step may comprise more than one ultrafiltration step using membranes with different MWCO, e.g. using two ultrafiltration separations wherein the first membrane has a higher MWCO than that of the second membrane. This arrangement may provide a better separation efficacy of the higher molecular weight components of the aqueous medium. After this separation step the permeate contains materials that have a molecular weight lower than the MWCO of the second membrane, including the sialylated oligosaccharide/sialylated lactose of interest.

In one embodiment, the aqueous medium, preferably a fermentation broth, is ultrafiltered using a membrane having a MWCO of 5-30 kDa, such as 10-25, 15 or 20 kDa.

Preferably, the pH of the fermentation broth or the enzymatic reaction mixture processed in the UF step is adjusted to around 4-5.5, e.g. around 5. This pH range offers a better performance of the UF step and higher recovery yield of the sialylated oligosaccharide/sialylated lactose, like sialylated lactoses, as it prevents the rearrangement to the corresponding fructose isomers in particular when the UF is performed at elevated temperature (vide infra), and in addition prevents inorganic precipitation during concentration.

In one embodiment, the ultrafiltration step is preceded by diluting the fermentation broth or the enzymatic reaction mixture. The UF step is conducted so that the degree of concentration (concentration factor, $CF_1$) is at least 1.25, more preferably at least 1.5. On the other hand, the $CF_1$ is advantageously not more than 4, preferably not more than 3.

The concentration factor ($CF_1$) in this UF step is the ratio of the volume (or mass) of the feed (which equals to that of the diluted broth) and that of the UF retentate (UFR). For example, when 50 kg of broth is diluted to 100 kg, which diluted broth is ultrafiltered, and 40 kg of permeate and 60 kg of retentate are collected, the $CF_1$ is 1.67. Exemplary $CF_1$ ranges of the UF step are 1.25-4, 1.25-3, 1.25-2.25, 1.5-4, 1.5-3, 1.5-2,25, 1.25-2 or 1.5-2. The UFR can be optionally washed with small amounts of water. In general, this UF step comprising a dilution of the broth prior to ultrafiltration and optionally washing the UFP with water is characterized with dilution factor ($DF_1$) of 1-3.5. The $DF_1$ in this step is calculated as the ratio of the total volume (or mass) of the UFP optionally combined with washing filtrate and that of the fermentation broth undiluted. For example, when 50 kg of broth is diluted to 100 kg, which diluted broth is ultrafiltered, and 70 kg of UFP and 30 kg UFR is collected, then the $DF_1$ is 1.4. Exemplary $DF_1$ ranges are 1.5-3.1, 1.8-3.1, 1-2.5, 1.5-2.5, 1.8-2.5, 2-3.1, 2-2.5, 2-2.3.

In other embodiment, the fermentation broth or the enzymatic reaction mixture as obtained (that is non-diluted) is ultrafiltered, the UF step is conducted so that the degree of concentration (concentration factor, $CF_2$) is at least 1.25, more preferably at least 1.5. On the other hand, the $CF_2$ is advantageously not more than 4, preferably not more than 3. The concentration factor in this UF step is the ratio of the volume (or mass) of the broth (which equals to that of the UF feed) and that of the UF retentate (UFR). For example, when 100 kg of broth is directly ultrafiltered and 40 kg of permeate and 60 kg of retentate are collected, the $CF_2$ is 1.67. Exemplary $CF_2$ ranges of the UF step are 1.25-4, 1.25-3, 1.25-2.25, 1.5-4, 1.5-3, 1.5-2.25, 1.25-2 or 1.5-2. Preferably, this step comprises a washing step of the UFR obtained in the OF step above, in order to improve the recovery yield of the sialylated oligosaccharide/sialylated lactose product. This step is performed by adding water, preferably purified water, to the UFR to give a suspension and the aqueous phase of the suspension is passed through the same UF membrane used in the above UF step to collect a washing filtrate of preferably the same volume (or mass) as that of the washing water applied. As a general rale, the higher the CF of the precedent UF step, the more the water added. In addition, the more the washing water, the more the additionally recovered product. However, above a certain volume of washing water no significantly more product can be washed out from the UFR. The washing water can be added in one portion or more subsequent portions, however it is favourable when the washing water is added continuously to the UFR with the same flow rate as the flow rate of the filtrate collection, to maintain a constant UFR concentrate volume. After the washing step, the UFP and the washing filtrate are combined for the next purification/isolation step(s). The combined UFP+washing filtrate fractions contain 85-96% of the sialylated oligosaccharide/sialylated lactose product of the fermentation broth (by mass when their dilution factor ($DF_2$) is 1 to 3.5, $DF_2$ in this step is calculated as the ratio of the total volume (or mass) of the UFP combined with washing filtrate and that of the undiluted fermentation broth (that equals to that of the UF feed). For example, when 100 kg of broth is directly ultrafiltered, 40 kg of UFP is collected, and the UFR is washed with 200 kg of water, then the $DF_2$ is 2.4. Exemplary $DF_2$ ranges are 1-3.1, 1.5-3.1, 1.8-3.1, 1-2.5, 1.5-2.5, 1.8-2.5, 2-3.1, 2-2.5, 2-2.3. Preferably, the application of more than 3-fold washing water volume or washing water mass (compared to the broth volume or mass before UF) does not significantly contribute to improving the recovery. On the other hand, the collection of higher volume of washing filtrate increases the technological time of the subsequent steps ii), iii) and iv). From technological point of view it is advantageous, when the volume (or mass) of the washing water used is around 1.5-2.5-fold, e.g. 1.6-1.9-fold, of that of the broth used in the UF step.

The UF step is, or the UF and washing steps are, conducted at constant temperature, preferably between 15 and 65° C., such as e.g. at 15-20 or at 55-65° C. Throughout this range a satisfactory recovery yield is available, however the higher the temperature, the higher the recovery yield. As a consequence, at higher temperature lower DF is sufficient to reach the same recovery yield. Preferably, at 55-65° C. a DF of around 2.0-2.3 ensures around 90% of recovery yield or even higher.

It should be emphasized that when applying a fermentation broth, no heat deactivation and disruption of the producing cell, or treating the cell with an agent (like Triton X) that make the cell wall more permeable, is necessary to apply in order to collect the intracellularly accumulated product.

2.3. Pre-Treatment of an Aqueous Medium Containing a Sialylated Oligosaccharide/Sialylated Lactose Before Ion Exchange Resin Treatment: Nanofiltration The pre-treatment of the aqueous medium containing the sialylated oligosaccharide/sialylated lactose may comprise a nanofiltration (NT) step. The NF step may follow the UF step or the optional step active charcoal treatment (vide infra). This nanofiltration step may advantageously be used to concentrate the previously treated aqueous medium containing the sialylated oligosaccharide/sialylated lactose and/ or to remove ions, mainly monovalent ions, and organic materials having a molecular weight lower than that of the sialylated oligosaccharide/sialylated lactose, such as monosaccharides. The nanofiltration membrane has a MWCO that ensures the retention of the sialylated oligosaccharide/sialylated lactose of interest, that is its MWCO is lower than that of the ultrafiltration membranes) used in step a), and around 25-50% of the molecular weight of the sialylated oligosaccharide/sialylated lactose. As an example, a nanofiltration membrane having a MWCO of about 150-300 Da is suitable for retaining sialylated lactose. In this regard the sialylated oligosaccharide/sialylated lactose is accumulated in the NF retentate (NFR). The nanofiltration can be combined with diafiltration with water in order to remove permeable molecules more effectively, e.g. until the conductivity of the permeate showing no or very low presence of salts.

The NF step according to this invention is conducted, with or without the optional diafiltration step, at constant temperature, preferably between 15-45° C., such as at 15-20° C. or at 35-45° C. This NF step, with or without diafiltration, is continued until reaching the desired concentration of the sialylated oligosaccharide/sialylated lactose in the NFR. Other technical parameters like setting in the flux and pressure is a matter of routine skills.

With the above disclosed NF step, at least 95% of the sialylated oligosaccharide/sialylated lactose obtained in the previous step can be retained.

In one preferred embodiment, the NF step follows the UF step, that is the UF permeate obtained in is nanofiltered and the NF retentate containing the produced sialylated oligosaccharide/sialylated lactose is collected and subjected to further separation/isolation steps.

2.4. Pre-Treatment of an Aqueous Medium or Aqueous Solution Containing a Sialylated Oligosaccharide/Sialylated Lactose Before Ion Exchange Resin Treatment: Active Charcoal Treatment Pre-treatment of an aqueous medium or aqueous solution containing a sialylated oligosaccharide/sialylated lactose may comprise an optional step of active charcoal (AC) treatment. The optional AC step may follow the UF step, NF step or the ion exchange resin treatment. The AC treatment helps to remove or at least reduce the amount of colorizing agents and/or water soluble contaminants, such as salts, if required.

A carbohydrate substance like a sialylated oligosaccharide/sialylated lactose of interest tends to be bound to the surface of charcoal particles from its aqueous solution, e.g. an aqueous solution obtained after the LT or NF step. Similarly, the colorizing agents also adsorb to the charcoal. While the carbohydrates and colour giving materials are adsorbed, water soluble materials not or weaker bound to the charcoal can be eluted with water. Changing the eluent from water to aqueous ethanol the adsorbed sialylated oligosaccharide/sialylated lactose can be easily eluted and collected in a separate fraction. The adsorbed colour giving substances would still remain adsorbed on the charcoal, thus decolourization and desalination can be achieved simultaneously. The charcoal treatment can be conducted by adding charcoal (e.g. powder, pellet or granulate) to the aqueous solution of the sialylated oligosaccharide/sialylated lactose under stirring, filtering off the charcoal, re-suspending in aqueous ethanol under stirring and separating the charcoal by filtration. In higher scale purification, the aqueous solution of the sialylated oligosaccharide/sialylated lactose after the UF step, NF step or ion exchange resin treatment is loaded to a column packed with charcoal, which may optionally be mixed with celite, then the column is washed with the required eluent. The fractions containing the sialylated oligosaccharide/sialylated lactose are collected. From these fractions, if necessary, the ethanol may be removed by e.g. evaporation to give an aqueous solution of the sialylated oligosaccharide/sialylated lactose.

Alternatively, under certain conditions, the sialylated oligosaccharide is not, or at least not substantially, adsorbed on the charcoal particles and elution with water gives rise to an aqueous solution of the sialylated oligosaccharide/sialylated lactose without its significant loss, meanwhile the colour giving substances remain adsorbed. To achieve this, the amount of activated charcoal applied for decolourization should be about 12-25% by mass relative to the sialylated oligosaccharide content of the feed solution obtained in a previous step, preferably about 15-20% relative to the sialyl lactose content of the feed solution. With this particular arrangement, as much as at least 90% of the sialylated oligosaccharide/sialylated lactose (by mass) obtained in the previous step can be collected back in the form of a decolourized solution.

Optionally, the charcoal bed can be washed with pure water to collect further amounts of sialylated oligosaccharide/sialylated lactose which is optionally bound to charcoal. The more the washing water applied, the more the additionally recovered product. However, above a certain volume of washing water no significantly more product can be washed out from the charcoal, and the chance of washing down already bound colour bodies is increasing. Therefore, to keep a trade-off between a maximum recovery yield and the dilution of the eluate, 16-25 l purified water/kg of charcoal is used in this washing step, preferably in at least two portions. This results in recovering further around 5% of sialylated oligosaccharide/sialylated lactose from charcoal (thus to reach at least 95% of accumulated recovery yield in this AC treatment step), whereas the obtained solution is colourless and the AC dilution factor is only around 1.4-1.9 (the AC dilution factor is calculated as the ratio of the volume (or mass) of charcoal treated combined eluents and that of feed solution). In one preferred embodiment, the active charcoal treatment is following the nanofiltration step, and is applied on the NF retentate.

2.5 Isolation of the Previously Separated and Purified a Sialylated Oligosaccharide/Sialylated Lactose Salt In the method of this invention for purifying a sialylated oligosaccharide/sialylated lactose, ultrafiltration is preferably conducted before any of the nanofiltration, active charcoal treatment and dual ion exchange treatment steps, and any of the nanofiltration, active charcoal treatment and dual ion exchange treatment steps can be applied in any order. A particularly preferred order is: UF, NF, AC treatment, dual ion exchange treatment.

After the above disclosed steps, the sialylated oligosaccharide/sialylated lactose so-obtained is provided in its salt form, preferably sodium salt form. If a solid form of the sialylated oligosaccharide/sialylated lactose salt is required, it can be spray-dried, freeze-dried or crystallized (provided if the sialylated oligosaccharide/sialylated lactose salt occurs in crystalline form, among sialylated oligosaccharide/sialylated lactose salts only some salts of 6'-SL have been reported as crystalline, see WO 2010/116317). Accordingly, the method of the invention may comprise one or more further steps, such as spray-drying an aqueous solution of the sialylated oligosaccharide/sialylated lactose salt obtained as disclosed above; or freeze-drying an aqueous solution of the sialylated oligosaccharide/sialylated lactose salt obtained as disclosed above; or crystallising a sialylated oligosaccharide/sialylated lactose salt from an aqueous solution obtained as disclosed above. Alternatively, the sialylated oligosaccharide/sialylated lactose salt may be provided in a form of a concentrated aqueous solution or syrup by removing water, e.g. by means of distillation, preferably vacuum distillation, or nanofiltration.

2.6 Production of the Aqueous Medium Containing a Sialylated Oligosaccharide/Sialylated Lactose The sialylated oligosaccharide/sialylated lactose can be produced in chemical synthesis, ex vivo enzymatic synthesis or by culturing a genetically modified capable of producing a sialylated oligosaccharide/sialylated lactose. The preferred method of producing a sialylated oligosaccharide/sialylated lactose is fermentation.

For chemical synthesis of 6'-SL see e.g. WO 2010/116317 or WO 2011/100979.

For ex vivo enzymatic synthesis of sialylated lactoses by using a transsialidase see e.g. Maru et al. *Biosci. Biotech. Biochem.* 56, 1557 (1992), Masuda et al. *J. Biosci. Bioeng.* 89, 119 (2000) or WO 2012/007588. For ex vivo enzymatic synthesis of 3'-SL by using a sialyl transferase see e.g. WO 96/32492, Gilbert et al. *Nature Biotechnol.* 16, 769 (1998), WO 99/31224 or Mine et al. *J. Carbohydr. Chem.* 29, 51 (2010).

The fermentative production comprising a genetically modified cell preferably occurs in the following way. An exogenously added acceptor is internalized from the culture medium into the cell where it is converted to the sialyl oligosaccharide of interest in a reaction comprising enzymatic sialylation mediated by an appropriate sialyl transferase. In one embodiment, the internalization can take place via a passive transport mechanism during which the exogenous acceptor diffuses passively across the plasma membrane of the cell. The flow is directed by the concentration difference in the extra- and intracellular space with respect to the acceptor molecule to be internalized, which acceptor is supposed to pass from the place of higher concentration to the zone of lower concentration tending towards equilibrium. In another embodiment, the exogenous acceptor can be internalized in the cell with the aid of an active transport mechanism, during which the exogenous acceptor diffuses across the plasma membrane of the cell under the influence of a transporter protein or permease of the cell. Lactose permease (LacY) has specificity towards mono- or disaccharide selected from galactose, N-acetyl-glucosamine, a galactosylated monosaccharide (such as lactose), an N-acetyl-glucosaminylated monosaccharide and glycosidic derivatives thereof. All these carbohydrate derivatives can be easily taken up by a cell having a LacY permease by means of an active transport and accumulate in the cell before being glycosylated (WO 01/04341, Fort et al. *J. Chem. Soc., Chem. Comm.* 2558 (2005), EP-A-1911850, WO 2013/182206, WO 2014/048439). This is because the cell is able to transport these carbohydrate acceptors into the cell using its LacY permease, and the cell lacks any enzymes that could degrade these acceptors, especially LacZ. The specificity towards the sugar moiety of the substrate to be internalized can be altered by mutation by means of known recombinant DNA techniques. In a preferred embodiment, the exogenously added acceptor is lactose, and its internalization takes place via an active transport mechanism mediated by a lactose permease of the cell, more preferably LacY. Being internalized in the cell, the acceptor is sialylated by means of a sialyl transferase expressed by a heterologous gene or nucleic acid sequence which is introduced into the cell by known techniques, e.g. by integrating it into the chromosome of the cell or using an expression vector. The genetically modified cell comprises a biosynthetic pathway to produce a sialic acid monosaccharide nucleotide donor (typically CMP-sialic acid) suitable to be transferred by the corresponding sialyl transferase. The genetically modified cell can produce CMP-sialic acid, in two ways. In one way, exogenously added sialic acid is internalized actively or passively, preferably actively by a sialic acid permease, more preferably by that encoded by nanT, and subsequently converted to CMP-sialic acid by a CMP-NeuAc synthase, e.g. encoded by a heterologous neuA. In another way, the internally available UDP-GlcNAc is utilized, by expressing heterologous neuC, neuB and neuR that convert it to CMP-sialic acid via ManNAc and sialic acid as intermediates. In the meantime, the cell's catabolic activity on sialic acid and its precursor is suppressed by inactivating/deletion of the aldolase gene (nanA) and/or the ManNAc kinase gene (nanK). The internalized carbohydrate precursor can be the subject of glycosylation other than sialylation, e.g. N-acetyl-glucosaminylation, galactosylation and/or fucosylation before being sialylated as described above.

In a preferred embodiment of the production of a sialylated oligosaccharide/sialylated lactoses by a genetically modified microorganism, the microorganism able to produce a sialylated oligosaccharide is an *E. coli*, preferably of LacY$^+$LacZ$^-$ genotype carrying neuBCA. The heterologous sialyltransferase gene in the microorganism is preferably an α-2,3- or an α-2,6-sialyl transferase with the aid of which, from the exogenously added lactose as carbohydrate acceptor, 3'-SL or 6'-SL is produced, respectively. Such a microorganism is disclosed e.g. in WO 2007/101862, Fierfort et al, *J. Biotechnol,* 134, 261 (2008), Drouillard et al. *Carbohydr. Res.* 345, 1394 (2010) and WO 2017/101958.

Accordingly, one embodiment of the present invention is a method for isolating a sialylated lactose from a fermentation broth obtained by culturing a genetically modified microorganism capable of producing said sialylated lactose from an internalized lactose, comprising the steps of
i) ultrafiltration of the broth to obtain an ultrafiltration permeate,
ii) nanofiltration of the ultrafiltration permeate to obtain a nanofiltration retentate,
iii) activated charcoal treatment of the nanofiltration retentate to obtain a decolorized aqueous solution, and
iv) treatment of the aqueous solution of step iii) with a strong anion exchange resin in chloride form and a strong cation exchange resin.

As a non-limiting example, the isolation yield of 6'-SL from its fermentation broth, produced in accordance with WO 2007/101862 or WO 2017/101958, has been improved by the following embodiment of the present method:
i) ultrafiltering the broth, preferably through a 15 kDa membrane, to obtain a OF permeate, followed by a water washing of the UF retentate, wherein the DF is 1.8-3.1, and preferably wherein the CF of the ultrafiltration is 1.25-2.25,
ii) nanofiltering, preferably with a 150-300 kDa membrane, the combined UF permeate and water washing filtrate to obtain an NF retentate,
iii) adding active charcoal to the NF retentate, preferably powdered active charcoal, more preferably in an amount of 12-25% by mass relative to the 6'-SL content of the NF retentate, to obtain a decolorized aqueous solution, and
iv) treating the decolorized solution with an ion exchange resin, which consist of the application of a strong acidic ion exchange resin
either in H$^+$ form followed by neutralization of the eluate with NaOH-solution,
or in Na$^+$-form,
and a strong anion exchange resin in Cl$^-$-form to give rise the sodium salt of 6'-SL.

In step iv), in a preferred embodiment, the application of a strong anion exchange resin in Cl$^-$-form is directly followed by that of a strong acidic ion exchange resin.

With the above procedure at least 70% of the 6'-SL produced by fermentation that precedes step i) can be isolated in the purified sodium salt form, wherein the overall inorganic anion contamination is not more than 1000 ppm, within which the multivalent anion content is below detection level, the overall cation content, excluding sodium, is below 500 ppm, preferably below 250 ppm, and the overall amino acid and organic amine content is below 100 ppm.

The above procedure can be applied to 3'-SL containing fermentation broth with the same performance.

EXAMPLES

Production of 6'-SL

6'-SL was produced by fermentation using *E. coli* of LacY$^+$LacZ$^-$ genotype having an α-2,6-sialyl transferase integrated in and expressed from its chromosome, and neuBCA and nadC expressed from the same plasmid, in accordance with WO 2017/101958.

Example 1 (Comparison Example)

A fermentation broth containing 6'-SL was ultrafiltered (15 kDa) at 60-65° C. to collect the UFP with a CF of 1.6-1.7. The UF retentate was then washed with purified water (1.5-2.5-fold volumes relative to the broth volume ultrafiltered) and the suspension was filtered through the same membrane to collect a washing filtrate. Analysis showed that 87-96% of 6'-SL contained in the broth was recovered in the combined UFP and washing filtrate.

The combined UFP and washing filtrate was nanofiltered applying a 150-300 Da membrane at 20-22 bars and 45° C. until the retentate showed a Brix of about 20-25. Analysis showed that 96% of 6'-SL contained in combined UFP and washing filtrate was recovered in the NF retentate.

To the above NF retentate (201 g solution containing 16.8 g of 6'-SL), powdered active charcoal was added (5 g), and the suspension was stirred for 1 hour. The charcoal was then filtered off and washed with distilled water (40 ml). The combined filtrate (231 g) was divided into two equal parts. The first solution was brought to the top of an Amberlite FPC 22 (H$^+$) ion exchange column (50 ml) and eluted followed by washing the column with distilled water (50 ml). To the eluate NaOH-solution was added (5M, 3.1 ml) to reach a pH of 6.7. The solution was freeze-dried to give 9.24 g of white powder of 6'-SL sodium salt. The second solution was brought to the top of an Amberlite FPC 22 (Na$^+$) ion exchange column (50 ml) and eluted followed by washing the column with distilled water (50 ml). The eluate was freeze-dried to give 9.27 g of white powder of 6'-SL sodium salt.

Assay (by IC): 82.9% (free acid), 90.8% (free acid as water free), 85.7% (Na-salt), 94.0% (Na-salt as water free). Assay (by NMR): 88.9% (free acid), 92.0% (Na-salt). Water content (by KF): 8.8%. Phosphate: 0.29%, orthophosphate: 0.90%, sulphate: 0.50%, potassium: 370 ppm, magnesium: 20 ppm, sodium: 3.49%.

Example 2

A fermentation broth containing 6'-SL was ultrafiltered and nanofiltered as disclosed in Example 1.

To the NF retentate (1751 g solution containing 36.5 kg of 6'-SL), powdered active charcoal was added (6.5 kg), and the suspension was stirred for 1 hour. The charcoal was then filtered off and washed with distilled water (three equal portions). The combined decolorized filtrates (3741) contained 34.4 kg of (92% recovery).

The above filtrate, in two portions, was brought to the top of a DIAION SA20A (CO ion exchange column (wet volume 110l). The eluent was directly brought to the top of an Amberlite FPC 22 (H$^+$) ion exchange column (wet volume 110l). The elution was continued with distilled water. To the eluate containing 6'-SL, 50% of NaOH-solution was added to reach a pH of 5.3. The above ion exchange set-up provided a purified solution of 6'-SL in sodium form (470l, 6'-SL recovery is 92%). The solution was then concentrated to its cca. ⅓ volumes by nanofiltration while the remaining sodium chloride was removed. Overall recovery yield was 72%.

A sample from the concentrated solution was freeze-dried and analysed:

Assay (by IC): 91.1% (free acid), 92.1% (free acid as water free), 94.25% (Na-salt), 95.3% (Na-salt as water free). Assay (by NMR): 90.6% (free acid), 93.8 (Na-salt), 94.8% (Na-salt as water free). Water content (by KF): 1.1%. Orthophosphate: <3 ppm, sulphate: <0.01%, chloride: 0.079%, potassium: 160 ppm, magnesium: <10 ppm, sodium: 3.25%.

The invention claimed is:

1. A method for obtaining a sialylated oligosaccharide from a fermentation broth, the method comprising:

filtering the fermentation broth by successive steps of ultrafiltration and nanofiltration;

contacting the filtered fermentation broth containing the sialylated oligosaccharide with a first exchange resin to obtain a first solution, and contacting the first solution with a second exchange resin to obtain a second solution comprising the sialylated oligosaccharide;

wherein the first exchange resin is a strong anion exchange resin in Cl– form or a strong cation exchange resin in alkali metal cation form, and when the first exchange resin is a strong anion exchange resin in Cl– form, the second exchange resin is a strong cation exchange resin, and when the first exchange resin is a strong cation exchange resin in alkali metal cation form, the second exchange resin is a strong anion exchange resin in Cl– form.

2. The method of claim 1, wherein the nanofiltration comprises performing nanofiltration on the product of the ultrafiltration step with a membrane comprising a 150-300 Da molecular weight cutoff.

3. The method of claim 1, wherein the ultrafiltration step comprises performing ultrafiltration with a membrane of 5-500 kDa.

4. The method of claim 1, wherein the strong cation exchange resin of the second exchange resin is in an alkali metal cation form or H$^+$-form.

5. The method of claim 1, wherein the yield of the sialylated oligosaccharide in the first solution is around 85% or greater than the sialylated oligosaccharide in the fermentation broth.

6. The method of claim 1, wherein the yield of the sialylated oligosaccharide in the second solution is more than 90% of the sialylated oliosaccharide in the first solution.

7. The method of claim 2, wherein said fermentation broth is obtained by culturing a genetically modified cell, wherein said cell is capable of producing said sialylated oligosaccharide from an internalized carbohydrate precursor.

8. The method of claim 1, wherein said sialylated oligosaccharide is a sialylated lactose.

9. The method of claim 8, wherein said sialylated lactose is 3'-SL or 6'-SL.

10. The method of claim 1, wherein said contacting of said first solution with said second exchange resin immediately follows contacting said aqueous medium with said first exchange resin.

11. The method of claim 7, wherein said genetically modified cell is from a genetically modified microorganism.

12. The method of claim 11, wherein said genetically modified microorganism is an *E. coli*, wherein the *E. coli* contains one or more characteristics selected from the group consisting of LacY+LacZ– genotype, a recombinant α-2,3- or α-2,6-sialyl transferase, and neuBCA genes.

13. A method for obtaining a sialylated oligosaccharide from a fermentation broth, the method comprising treating the fermentation broth via ultrafiltration, nanofiltration, and, optionally, an active charcoal treatment, to result in an aqueous solution containing said sialylated oligosaccharide; and contacting the aqueous solution with a first exchange resin to obtain a first solution, and contacting the first solution with a second exchange resin to obtain a second solution comprising the sialylated oligosaccharide;

wherein, the first exchange resin is a strong anion exchange resin in Cl– form, a strong cation exchange resin in H+ form, or a strong cation exchange resin in alkali metal cation form, and when the first exchange resin is a strong anion exchange resin in Cl− form, the second exchange resin is a strong cation exchange resin, when the first exchange resin is a strong cation exchange resin in H+ form, the second exchange resin is a strong anion exchange resin in Cl− form and the first solution is neutralized before contacting the second exchange resin, and when the first exchange resin is a strong cation exchange resin in alkali metal cation form, the second exchange resin is a strong anion exchange resin in Cl− form.

14. The method of claim 13, wherein the yield of the sialylated oligosaccharide in the first solution is around 85% or greater than the sialylated oligosaccharide in the fermentation broth.

15. The method of claim 13, wherein the obtained sialylated oligosaccharide is in the form of its alkali metal salt.

16. The method of claim 13, wherein the first exchange resin is a strong cation exchange resin in H+ form.

17. The method of claim 13, wherein the yield of the sialylated oligosaccharide in the second solution is more than 90% of the sialylated oliosaccharide in the first solution.

18. The method of claim 13, wherein the first exchange resin is a strong cation exchange resin in alkali metal cation form.

19. The method of claim 13, wherein treating the aqueous medium comprises the ordered steps of ultrafiltration, nanofiltration and active charcoal treatment.

20. The method of claim 13, wherein said fermentation broth is obtained by culturing a genetically modified cell, wherein said cell is capable of producing said sialylated oligosaccharide from an internalized carbohydrate precursor.

21. The method of claim 13, wherein said sialylated oligosaccharide is a sialylated lactose.

22. The method of claim 21, wherein said sialylated lactose is 3'-SL or 6'-SL.

23. The method of claim 13, wherein said contacting of said first solution with said second exchange resin immediately follows contacting said fermentation broth with said first exchange resin.

24. The method of claim 20, wherein said genetically modified cell is from a genetically modified microorganism.

25. The method of claim 24, wherein said genetically modified microorganism is an *E. coli*, wherein the *E. coli* contains one or more characteristics selected from the group consisting of LacY+LacZ− genotype, a recombinant α-2,3- or α-2,6-sialyl transferase, and neuBCA genes.

* * * * *